United States Patent [19]

Tsukamoto et al.

[11] 4,360,464

[45] Nov. 23, 1982

[54] PROCESS FOR PRODUCTION OF 1-ARYLOXY-AMINOPROPANE DERIVATIVES

[75] Inventors: Kunio Tsukamoto, Chofu Mine; Yasushi Suzuki, Yokohama; Akihiro Izumi, Kawasaki; Yoshio Hiramatsu, Tokyo, all of Japan

[73] Assignee: Teikoku Hormone Mfg. Co. Ltd., Tokyo, Japan

[21] Appl. No.: 913,238

[22] Filed: Jun. 6, 1978

Related U.S. Application Data

[60] Division of Ser. No. 828,740, Aug. 29, 1977, abandoned, which is a continuation of Ser. No. 92,252, Nov. 23, 1970, abandoned.

[30] Foreign Application Priority Data

| Nov. 28, 1969 | [JP] | Japan | 44-95027 |
| Mar. 31, 1970 | [JP] | Japan | 45-26548 |
| Mar. 31, 1970 | [JP] | Japan | 45-26549 |
| Jul. 21, 1970 | [JP] | Japan | 45-63377 |

[51] Int. Cl.$^3$ .................. C07D 207/24; C07D 317/06
[52] U.S. Cl. ..................................... 548/490; 549/366
[58] Field of Search ............ 260/340.5 L, 340.6, 260/570.7, 326.15

[56] References Cited

U.S. PATENT DOCUMENTS

| 3,415,873 | 12/1968 | Stevens | 260/570.7 X |
| 3,432,545 | 3/1969 | Howe | 260/570.7 X |
| 3,501,769 | 3/1970 | Crowther et al. | 260/570.7 X |
| 3,551,493 | 12/1970 | Ruschig et al. | 260/570.7 |

OTHER PUBLICATIONS

Gaertner, "Journal of Heterocyclic Chemistry", vol. 6, No. 3, pp. 273-277, (1969).

*Primary Examiner*—Robert V. Hines
*Attorney, Agent, or Firm*—Sherman & Shalloway

[57] ABSTRACT

A process for the preparation of 1-aryloxy-3-aminopropane derivatives and acid addition salts thereof and such products per se the process comprising ring opening of tertiary azetidinol derivatives. They possess $\beta$-adrenergic blocking activity and an activity of controlling secretion of gastric juice and are therefore useful antiulcerative medicines for peptic ulcer and duodenal ulcer.

12 Claims, No Drawings

PROCESS FOR PRODUCTION OF 1-ARYLOXY-AMINOPROPANE DERIVATIVES

This is a division, of application Ser. No. 828,740, filed and now abandoned Aug. 29, 1977 which in turn is a continuation of application Ser. No. 92,252 filed Nov. 23, 1970, now abandoned.

This invention relates to a process for the preparation of 1-aryloxy-3-aminopropane derivatives by ring opening of tertiary azetidinol derivatives and to certain novel derivatives per se.

It has been known that 1-amino-3-aryloxy-2-propanol derivatives having an alkyl substituent such as an isopropyl group at the N-position may be prepared by reacting 1-aryloxy-2,3-epoxypropane or 1-aryloxy-3-halogeno-2-propanol with a primary amine having a branched alkyl group such as an isopropyl group, and that the acid addition salts of such derivatives possess $\beta$-adrenergic blocking activity (see, for instance, the specification of Belgian Pat. No. 641,133).

As a result of the present invention 1-aryloxy-3-aminopropane derivatives expressed by the following formula:

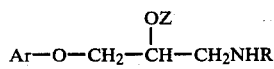

Ar—O—CH$_2$—CH—CH$_2$NHR    (I)

(with OZ on the CH)

wherein Ar is a substituted or unsubstituted aryl group, Z is a hydrogen atom or a protective group bonded to the oxygen atom by an aliphatic ether linkage, and R is an alkyl or aralkyl group, have now been obtained by reacting a tertiary azetidinol derivative expressed by the following formula:

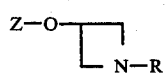

(II)

wherein Z and R are as defined above, with a compound expressed by the following formula Ar—OH    (III)

wherein Ar is as defined above, in the non-aqueous reaction system.

Although some of the tertiary azetidinol derivatives expressed by above formula (II) are known substances, it has not been known that ring opening of these tertiary azetidinol derivatives with phenols or naphthols, especially alkyl-substituted phenols or naphthols, results in formation of aryloxy derivatives.

With regard to the ring opening reaction of azetidine derivatives, it has been known that when a quaternary azetidinium cation is reacted with an alkali phenolate in the aqueous medium, the cleavage occurs in the quaternary azetidinium cation to form a 1-aryloxy-3-N,N-dialkyl-2-propanol. (see J. Org. Chem., 33, 523–530 (1968) and Tetrahedron Letters (1967) 343–347).

Even if the above reaction is applied to tertiary azetidinol derivatives, it is difficult to obtain the intended 1-aryloxy-3-N-monoalkyl-2-propanols. Unexpectedly, it has now been found that when tertiary azetidinol derivatives are reacted with phenols or naphthols, the ring opening occurs in the tertiary azetidinol derivatives and 1-aryloxy-3-N-monoalkyl-2-propanol derivatives are formed.

Tertiary Azetidinol Derivatives

In the tertiary azetidinol derivatives expressed by the above formula (II), it is preferred that the group R is an alkyl group of up to 13 carbon atoms, especially up to 6 carbon atoms, or an aralkyl group of 7 to 9 carbon atoms.

As the tertiary azetidinol derivative, N-alkyl-(secondary)-tertiary azetidinols of the following formula

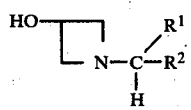

(II-a)

in which R$^1$ and R$^2$, which may be the same or different, are a hydrogen atom or an alkyl group of 1 to 4 carbon atoms, such as 1-(iso-propyl)-3-azetidinol, 1-(sec.-butyl)-3-azetidinol and 1-(sec.-amyl)-3-azetidinol; and N-tertiary alkyltertiary azetidinol derivatives of the following formula

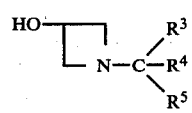

(II-b)

in which R$^3$, R$^4$ and R$^5$, which may be the same or different, are an alkyl group of 1 to 4 carbon atoms, such as 1-(tert.-butyl)-3-azetidinol and 1-(tert.-amyl)-3-azetidinol may be cited.

In addition to such tertiary azetidinols having a branched alkyl group, 1-ethyl-3-azetidinol and 1-benzyl-3-azetidinol may be used.

Preferable examples of tertiary azetidinol derivatives, whose hydroxyl group is protected, are those expressed by the following formula

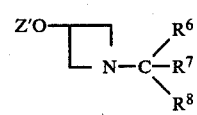

(II-c)

in which R$^6$, R$^7$ and R$^8$, which may be the same or different, are a hydrogen atom or an alkyl group of 1 to 4 carbon atoms, preferably at least two of R$^6$, R$^7$ and R$^8$ being alkyl groups, and Z' is a group

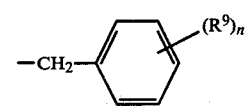

(in which R$^9$ is a hydrogen atom or an electron-donor group such as an alkoxy group of up to 4 carbon atoms, e.g., methoxy, ethoxy, and propoxy, an alkyl group of up to 4 carbon atoms, e.g., methyl, ethyl, n-propyl and iso-propyl, a halogen atom, e.g., chlorine and bromine, and a halogenated alkyl, e.g., trifluoromethyl; and n is a number of 1 to 3), or an alkoxymethyl group which has up to 4 carbon atoms in the alkyl portion.

As such hydroxyl-protected tertiary azetidinol derivatives to be used in this invention, the following may be exemplified 3-benzyloxy-1-methylazetidine, 3-(p-methoxybenzyloxy)-1-methylazetidine, 3-(p-ethoxybenzyloxy)-1-methylazetidine, 3-(p-methylbenzyloxy)-1-methylazetidine, 3-(p-etylbenzyloxy)-1-methylazetidine, 3-(p-chlorobenzyloxy)-1-methylazetidine, 3-benzyloxy-1-ethyl-azetidine, 3-(p-methoxybenzyloxy)-1-ethylazetidine, 3-(p-ethoxybenzyloxy)-1-ethylazetidine, 3-(p-methylbenzyloxy)-1-ethylazetidine, 3-(p-ethylbenzyloxy)-1-ethylazetidine, 3-(p-chlorobenzyloxy)-1-ethylazetidine, 3-(o-methoxybenzyloxy)-1-ethylazetidine, 3-benzyloxy-1-propylazetidine, 3-benzyloxy-1-(iso-propyl)azetidine, 3-(p-methoxybenzyloxy)-1-(iso-propyl)azetidine, 3-(p-ethoxybenzyloxy)-1-(iso-propyl)azetidine, 3-(p-methylbenzyloxy)-1-(iso-propyl) azetidine, 3-(p-ethylbenzyloxy)-1-(iso-propyl)azetidine, 3-(p-chlorobenzyloxy)-1-(iso-propyl)azetidine, 3-benzyloxy-1-(tert.-butyl)azetidine, 3-(p-methoxybenzyloxy)-1-(tert.-butyl) azetidine, 3-(p-ethoxybenzyloxy)-1-(tert.-butyl)azetidine, 3-(p-methylbenzyloxy)-1-(tert.-butyl)azetidine, 3-(p-chlorobenzyloxy)-1-(tert.-butyl)azetidine, 3-benzyloxy-1-benzylazetidine, 3-benzyloxy-1-phenetylazetidine, 3-methoxymethoxy-1-benzylazetidine, 3-ethoxymethoxy-1-benzylazetidine, 3-n-propoxymethoxy-1-benzylazetidine, 3-iso-propoxymethoxy-1-benzylazetidine, 3-methoxymethoxy-1-iso-propylazetidine, 3-methoxymethoxy-1-tert.-butylazetidine, 3-(tert.-butoxymethoxy)-1-benzylazetidine, 3-(tert.-butoxymethoxy)-iso-propylazetidine, 3-(tert.-butoxymethoxy)-1-tert.-butylazetidine, 3-(tert.-butoxy)-1-benzylazetidine, 3-(tert.-butoxy)-1-iso-propylazetidine, 3-(tert.-butoxy)-1-tert.-butylazetidine, 3-(tert.-amyloxy)-1-benzylazetidine, 3-tert.-amyloxy-1-iso-propylazetidine, 3-(tert.-amyloxy)-1-tert.-butylazetidine and 3-(tert.-amyloxy)-1-tert.-amylazetidine.

Among compounds expressed by the above formula (II), those in which Z stands for a substituted on unsubstituted benzyl group are heretofore unknown novel compounds. These novel compounds may be synthesized by reacting a compound of the following formula

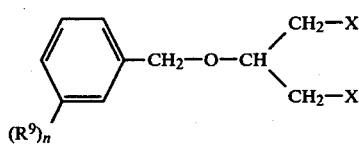

in which X is a halogen atom or a reactive ester residue, $R^9$ is a hydrogen atom or an electrondonor group, and n is an integer of 1 to 3, with a primary amine of the following formula

in which R is an alkyl or aralkyl group.

The compounds of the above formula (IV) used as starting compounds in this invention are compounds known per se. In the above formula (IV), the group $R^9$ may be a hydrogen atom or an electron-donor group such as an alkoxy group of up to 4 carbon atoms, e.g., methoxy, ethoxy and propoxy, an alkyl group, e.g., methyl, ethyl, n-propyl and iso-propyl, a halogen atom, e.g., chlorine and bromine, and a halogenated alkyl group, e.g., trifluoromethyl group. When the benzene nucleus is substituted by an electron-donor group, it is preferred that the substituent exists in the para- or ortho-position.

The compounds of the above formula (IV) to be used as starting compounds in this invention include, for example, 1,3-dichloro-2-(benzyloxy)propane, 1,3-dibromo-2-(benzyloxy) propane, 1,3-dichloro-2-(p-methoxybenzyloxy)propane, 1,3-dibromo-2-(p-methoxybenzyloxy)propane, 1,3-dichloro-2-(p-ethoxybenzyloxy)propane, 1,3-dibromo-2-(p-ethoxybenzyloxy) propane, 1,3-dichloro-2-(o-methoxybenzyloxy)propane, 1,3-dibromo-2-(o-methoxybenzyloxy)propane, 1,3-dichloro-2-(ethoxybenzyloxy)propane, 1,3-dibromo-2-(o-ethoxybenzyloxy)propane, 1,3-dichloro-2-(p-methylbenzyloxy)propane, 1,3-dibromo-2-(p-methylbenzyloxy)propane, 1,3-dichloro-2-(p-ethylbenzyloxy) propane, 1,3-dibriomo-2-(p-ethylbenzyloxy)propane, 1,3-dichloro-2-(p-iso-propylbenzyloxy)propane, 1,3-dichloro-2-(p-chlorobenzyloxy)propane and 1,3-dibromo-2-(p-chlorobenzyloxy)propane.

As the primary amine of general formula (V) there primary alkylamines and primary arylamines may be used. It is preferred that in the formula (V), the group R is a lower alkyl group such as methyl, ethyl, n-propyl, iso-propyl, n-butyl, iso-butyl, sec.-butyl and tert.-butyl, or an aralkyl group such as benzyl phenethyl. Either primary amines of less steric hindrance such as methyl amine and ethylamine or primary amines of more steric hindrance such as tert.-butylamine, isopropylamine and benzylamine may be used in this invention, and from either of these amines azetidine derivatives of formula (II) can be obtained in good yields. This is one of the prominent advantages of this invention.

The reaction between the compound of formula (IV) and the primary amine of formula (V) may be conducted in the absence of a solvent, but in order to obtain azetidine derivatives of formula (II) in high yields, while preventing formation of diamines and polymers as by-products it is preferable to conduct the reaction in an inert liquid medium. Water is used most preferably as the inert liquid medium. The use of water as a reaction medium results in the formation of azetidine derivatives of formula (II) in very high yields. Instead of water, a mixed liquid of water and a water-miscible organic solvent such as an alcohol, e.g., methyl alcohol, ethyl alcohol and ethylene glycol, and tetrahydrofuran may be used. Aromatic solvents such as benzene, toluene and aromatic alcohol solutions may be also used, but the time required for the reaction is very long.

Primary amines of formula (V) may be added to the reaction system in the form of an aqueous solution, and the reaction may be advanced in the state where compounds of formula (IV) are dispersed in such an aqueous solution. In general, it is preferable to use the primary amine of formula (V) in an amount exceeding the stoichiometric amount, for instance, B 2 to 5 moles per mole of the compound of formula (IV). In such a case, unexpectedly, the formation of diamines as by-products is extremely reduced. The excess amine is recovered by a customary method. When the primary amine of formula (V) is used in an excess amount, it is unnecessary to add an acid binder to the reaction system, but it is possible to add an acid binder such as a tertiary amine, pyridine and an inorganic alkali.

The reaction temperature is not critical, but in order to shorten the reaction time, it is preferable to conduct the reaction at a temperature from 60° to 100° C. At such a temperature, the reaction is usually completed in 10 to 50 hours.

In accordance with this invention, a process is provided for the preparation of azetidinol derivatives of the following formula

wherein R is an alkyl group, comprising reducing an azetidine derivative of the following formula, which is prepared by the above-mentioned reaction,

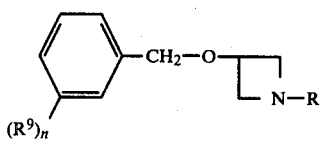

wherein R, $R^9$ and are as defined above, with hydrogen.

The hydrogen reduction may be accomplished at a temperature ranging from room temperature to 100° C. under a hydrogen pressure of 1 to 100 atmospheres with a metallic catalyst such as Raney nickel, Raney cobalt, U-nickel, palladium and platinum.

In compounds of formula (II-d), it is not always easy to selectively isolate the benzyl group alone because of the reactivity of the azetidine ring and the steric hindrance due to the benzyl and alkyl groups. Accordingly, it is difficult to split off the benzyl group with a mineral acid. When a palladium-carbon catalyst is used, the reaction conducted under room temperature and atmospheric conditions results substantially in mere recovery of the starting material. Accordingly, in the case of a palladium-carbon catalyst, considerably severe reaction conditions are required. The catalysts that can advance advantageously the hydrogen reduction under relatively mild conditions are Raney nickel and U-nickel.

Phenols and naphthols

Any optional substituted or unsubstituted phenols and naphthols may be used as compounds expressed by the general formula (III), Ar—OH. As such phenols and naphthols those preferably used are expressed by the following formula

(III-a)

wherein $R^{10}$, $R^{11}$ and $R^{12}$, which may be the same or different, are a hydrogen atom, an alkyl or alkenyl group of 1 to 4 carbon atoms, an alkoxy group of 1 to 4 carbon atoms, a hydroxyl group or an amino group, $R^{10}$ and $R^{11}$ may be bonded to each other to form an alkylene or ketoalkylene group, or they may form a 5- or 6-membered heterocyclic ring via hetero atoms, and Ar' is a benzene or naphthalene ring.

Particularly preferable examples of the phenols or naphthols expressed by formula (III) are 2,3-xylenol, 2,3-diethylphenol, 2-ethyl-3-methylphenol, tetrahydronaphthol, α-naphthol and β-naphthol.

Polyhydric phenols and naphthols and multifunctional phenols and naphthols such as aminophenols and aminonaphthols may also be used as the phenol or naphthol of formula (III) in this invention. Surprisingly, when these polyfunctional phenols and naphthols are used, only one phenolic hydroxyl group reacts with the azetidinol derivatives of formula (II) to give the intended compound. In the conventional method, by which an epoxy or epihalohydrin compound is reacted with a phenol or naphthol, functional groups other than the hydroxyl group to be reacted should be protected with suitable protective groups before the initiation of the reaction and these protective groups should be split off after the reaction. However, in this invention, it is quite unnecessary to conduct such troublesome steps for introduction and splitting-off of protective groups. This is one of the advantages of this invention.

As such phenols and naphthols, p-hydroquinone, 2,3-dimethyl-1,4-hydroquinone, 1-dihydroxynaphthalene, 1,5-dihydroxynaphthalene, 6-methoxy-1-naphthol, 4-methoxy-2,3-dimethylphenol, p-aminophenol, m-aminophenol, 5-oxo-5,6,7,8-tetrahydronaphth-1-ol, 5-oxo-5,6,7,8-tetrahydronaphth-2-ol, 5-hydroxyindol and 5-hydroxy-1,4-benzioxene may be cited.

Reaction Conditions

In accordance with this invention, tertiary azetidinol derivatives of the general formula (II) are reacted with phenols or naphthols expressed by the general formula (III) in the non-aqueous reaction system.

It is preferable to conduct the reaction in the absence of a solvent or in a non-polar solvent such as benzene, xylene and ether. In general, the reaction is effected at a temperature from 130° to 250° C., preferable temperatures being in the range from 150° to 180° C. The reaction may be carried out under atmospheric or elevated pressure. It is possible to use a catalyst, for instance, a basic catalyst such as solid caustic potash, caustic soda, triethylamine or other alkaline substance.

In one of the preferable embodiments of this invention, the reaction is carried out while keeping both the tertiary azetidinol derivatives of formula (II) and the phenols or naphthols of formula (III) in the molten state, in the presence of 1/100 to 1/10 mole per mole of the phenol or naphthol of a solid caustic alkali. In this embodiment, it is advantageous to use the phenol or naphthol in an amount slightly in excess based on the tertiary azetidinol, for instance, more than 1.1 moles, preferably about 1.2 moles, per mole of the tertiary azetidinol derivative.

As a result, 1-aryloxy-3-aminopropane derivatives of the following formula

are obtained in accordance with the process of this invention.

The product can be obtained by distillation in the form of a free base. It is also possible to recover the intended product in the form of an acid addition salt.

As the acid addition salts of compounds of the above formula (I), the following may be cited: salts of inorganic acids such as hydrochloric acid, hydrobromic acid and sulfuric acid, and organic acids such as succinic acid, tartaric acid and salicylic acid. The acid addition salts can be easily recovered by adding the above-mentioned acids to the resulting bases of N-substituted aminoalcohols.

According to the process of this invention, by using azetidinol derivatives of formula (II) as the starting material, it is possible to obtain N-substituted aminoalcohols of formula (I) in high yields even if azetidinols and phenols or naphthols are reacted in stoichiometric amounts. On the other hand, in the conventional process, when epoxide or halohydrin compounds are used as starting material, in order to control polymerization of the epoxide or halohydrin compounds and formation of di-substituted products, it is necessary to use expensive amines in a great excess. Accordingly, it is apparent that the process of this invention which can give N-substituted aminoalcohols of high purity without occurrence of undesired side reactions by using stoichiometric amounts of reactants has various advantages over such conventional processes.

Further, in the conventional process comprising reacting a 3-substituted-amino-1-halogeno-2-propanol or 3-substituted-1,2-opoxypropane with a substituted phenol or naphthol and thus forming an aryloxyalkanolamine derivative, in order to prevent occurrence of undesired side reactions and improve the yield of the desired product, it is necessary to protect the hydrogen of the secondary amine with a protective group prior to the reaction, conduct the aryloxylation and split off the protective group after the reaction. On the other hand, the process of this invention makes it possible to obtain intended products from azetidinol derivatives by one step in high yields, and in view of the structure of the starting compounds, it is apparent that in the process of this invention it is quite unnecessary to conduct such troublesome operations of introducing and splitting off protective groups.

Utility

Among the intended compounds of this invention, those having a free hydroxyl group, particularly the derivatives expressed by the following formula

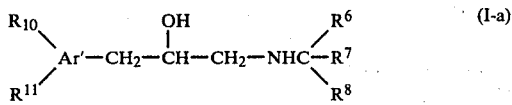

wherein Ar', $R^6$, $R^7$, $R^8$, $R^{10}$ and $R^{11}$ are as defined above, such as 1-(tert.-butylamino)-3-(2',3'-dimethylphenoxy)-2-propanol, 1-(tert.-butylamino)-3-(2'-ethyl-3'-methylphenoxy)-2-propanol, 1-(tert.-butylamino)-3-(2',3'-diethylphenoxy)-2-propanol, 1-(tert.-amylamino)-3-(2',3'-dimethylphenoxy)-2-propanol, 1-(α-naphthoxy)-3-(tert.-butylamino)-2-propanol, 1-(β-naphthoxy)-3-(tert.-butylamino)-2-propanol, 1-(α-naphthoxy)-3-(isopropylamino)-2-propanol and 1-(5',6',7',8'-tetrahydro-1-naphthoxy)-3-(tert.-butylamino)-2-propanol, and hydrochlorides of these derivatives are useful as β-adrenergic blocking medicines in the treatment or prophylaxis of coronary artery diseases such as angina pectoris and cardiac arrhythmias.

Further, the novel compounds of the following formula obtained by the process of this invention

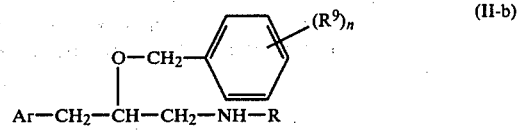

wherein Ar, R, $R^9$, and n are as defined above, are useful as intermediates leading to the above-mentioned compounds of formula (I-a), and moreover, they possess an activity of controlling secretion of gastric juice and are therefore useful antiulcerative medicines for peptic ulcers and duodenal ulcers.

Splitting-Off of Protective Groups I

In accordance with this invention, a process is provided for the preparation of 3-aryloxy-1-amino-2-propanols expressed by the following formula

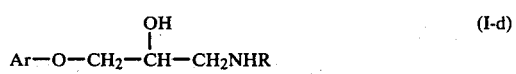

wherein R and Ar are as defined above, which comprises splitting off a protective group $Z^1$ from a 3-aryloxy-1-amino-propane derivative expressed by the following formula

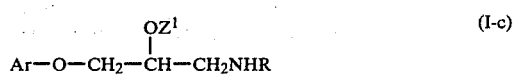

wherein R, $Z^1$ and Ar are as defined above, by a method known per se.

The splitting-off of the protective group may be performed by a method known per se, such as hydrogen reduction, acid hydrolysis and thermal decomposition. A suitable method of the splitting-off of the protective group may be chosen depending on the kind of protective group. For instance, in the case that the protective group is an aralkyl or alkoxyalkyl group, hydrogen reduction is advantageously adopted. In this case, the hydrogen reduction may be performed at a temperature ranging from room temperature to 100° C. with a calculated amount of hydrogen of atmospheric pressure in the presence of a metallic catalyst, for instance, Raney nickel, Raney cobalt, U-nickel, palladium or platinum. In the above reaction, the splitting-off of the protective group $Z^1$ from compounds of formula (I-c) advances sufficiently under room temperature and atmospheric conditions, and the intended compounds of formula (I-d) can be obtained.

Splitting-Off of Protective Groups II

It has now been found that when 1-aryloxy-3-aminopropane derivatives expressed by the following formula

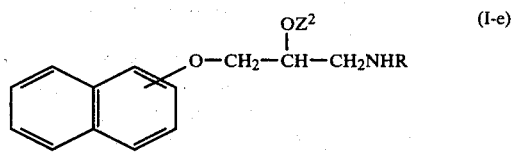

wherein R is as defined above and $Z^2$ is a group

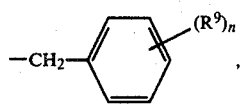

are hydrogenated under elevated pressure in an organic solvent in the presence of a hydrogenation catalyst, 1-aryloxy-3-amino-2-propanol derivatives expressed by the following formula

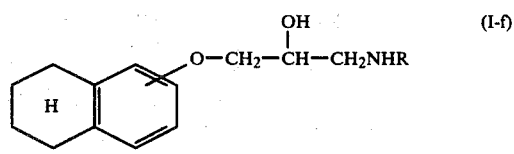

wherein R is as defined above, can be obtained in almost quantitative yields.

The hydrogenation of derivatives of the above formula (I-e) is conducted under hydrogen pressure in an organic solvent in the presence of a hydrogenation catalyst.

Any organic solvent may be used as long as it is capable of dissolving the derivatives of formula (I-3) and inert to the reaction. For instance, alcohols such as methanol, ethanol and propanol, ethers such as ethyl ether and tetrahydrofuran, N,N-dialkylamides such as dimethylformamide and dimethylacetamide and carboxylic acids such as acetic acid may be cited. Most preferable solvents are alcohols. Derivatives of formula (I-3) are usually liquid, but in the absence of a solvent, the hydrogenation hardly advances and merely results in recovery of starting compounds.

Aromatic-hydrogenation catalysts are usually used as the hydrogenation catalyst. For instance, Raney metal catalysts such as Raney nickel and Raney cobalt are preferably used. These catalysts are used in catalytic amounts usually adopted for an ordinary hydrogenation reaction. For instance, they may be used in an amount of $\frac{1}{2}$ to $\frac{1}{2}$ of the starting compounds on a weight basis.

In this invention, to conduct the hydrogenation under hydrogen pressure is quite important for attaining coincidentally the reduction of one naphthalene ring of the intermediate of formula (I-e) and the splitting-off of the benzyl group. When the hydrogenation is conducted under atmospheric pressure, a mixture of a compound in which the 5, 6, 7, 8 position of naphthalene ring is reduced without splitting-off of the benzyl group is obtained and a compound in which only the benzyl group is splitted off without reducing 5, 6, 7, 8 position of naphthalene ring is obtained, and the intended 1-tetrahydro-naphthyloxy-3-amino-2-propanol derivative of general formula (I-f) cannot be obtained in a purified form.

The pressure of hydrogen may be varied depending on the kind of catalyst used and the reaction temperature, but in general, it is preferable to use hydrogen of 2–100 kg/cm² gauge, especially 50–80 kg/cm² gauge. The reaction temperature is in the range from room temperature to 100° C., preferably from 40° to 50° C.

When the hydrogenation is carried out under the above-mentioned reaction conditions in accordance with this invention, the hydrogenation of one ring of naphthalene of the intermediate of formula (I-e), the one not bonded, to oxygen.

and the splitting-off of the benzyl group concurrently occur in one step; and 1-tetrahydronaphthyloxy-3-amino-2-propanol derivatives of formula (I-f) can be obtained almost quantitatively in yields of 90% or more, and these intended products are characterized by very high purity. Thus, it is another advantage of this invention that the intended products of formula (I-f) can be generally obtained directly in the form of crystals. Of course, it is possible to recover these products in the form of an acid addition salt by utilizing a customary technique known per se.

Conventionally, 1-tetrahydronaphthyloxy-3-amino-2-propanol derivatives of formula (I-f), which are useful as β-adrenergic blocking agents, have been prepared by a method comprising subjecting the corresponding 1-naphthyloxy-3-amino-2-propanol derivatives to hydrogenation (see, for instance, Japanese Patent Publication No. 10824/67). In such a method, however, an expensive catalyst of high hydrogenation activity such as palladium black and rhodium black should be used, and the hydrogenation should be conducted under such severe conditions as hydrogen pressure of 145 atmospheres and 132° C. In this invention, however, by using novel benzyloxy derivatives of above formula (I-e) as intermediates, it is possible to obtain the intended products of formula (I-f) in high yields and with high purity under milder conditions, as illustrated in the examples given hereinbelow.

This invention will now be described by referring to examples but this invention is not limited by these examples at all.

EXAMPLE 1

To a mixture of 6.5 parts of 1-(tert.-butyl)-3-azetidinol and 6.7 parts of 2,3-xylenol 0.2 part of potassium hydroxide was added, and the mixture was heated at 155° C. for 20 hours. The reaction mixture was cooled and then dissolved in 100 parts of ether. The solution was washed three times with 50 parts of 2 N-sodium hydroxide aqueous solution and extracted three times with 2 N-hydrochloric acid aqueous solution. The extract was washed with 50 parts of ether and was made alkaline by adding 2 N-sodium hydroxide solution gradually thereto. Then, the ether extraction was conducted three times and the extract was condensed and allowed to stand in a cool place. As a result, crystals were formed which were recrystallized twice from ether to yield 8.3 parts of 1-(2', 3'-dimethylphenyloxy)-3-(tert.-butylamino)-2-propanol having a melting point of 57° C. Results of infra-red spectrum analysis and ultraviolet ray absorption analysis of the product are as follows:

IR $\nu_{max}^{KBr}$ (cm$^{-1}$): 3400, 3250, 2960, 2910, 1455, 1100, 770

UV $\lambda_{max}^{EtOH}$ $m\mu(\epsilon)$: 271.2(1.08×10³) 274(1.07×10³) 279.3(1.11×10³)

EXAMPLE 2

To a mixture of 6.5 parts of 1-(tert.butyl)-3-azetidinol and 6.7 parts of 2,3-xylenol 0.2 part of sodium hydroxide was added, and the mixture was heated at 160° C. for 24 hours. The reaction mixture was cooled and then dissolved in 100 parts of ether. The solution was washed twice with 50 parts of 2 N-sodium hydroxide aqueous solution and extracted three times with 50 parts of 2 N-hydrochloric acid aqueous solution. The extract was washed with 50 parts of ether and was made alkaline by addition of 2 N-sodium hydroxide aqueous solution. The solution was cooled and agitated to form crystals.

The resulting crystals were dried and recrystallized twice from ether to yield 9.2 parts of 1-(2',3'-dimethylphenyloxy)-3-(tert.-butylamino)-2-propanol having a melting point of 57° C.

EXAMPLE 3

Preparation of 1-(2-propenylphenoxy)-3-(tert.-butylamino)-2-propanol hydrochloride To a mixture of 6.5 parts of 1-(tert.-butyl)-3-azetidinol and 7.4 parts of 2-propenylphenol 0.2 part of potassium hydroxide was added, and the mixture was heated under nitrogen gas at 150° C. for 22 hours. The reaction mixture was cooled and then dissolved in 100 parts of ether. The solution was washed twice with 50 parts of 2 N-sodium hydroxide aqueous solution and then extracted three times with 50 parts of 2 N-hydrochloric acid aqueous solution. The extract was washed with 50 parts of ether and made alkaline by addition of 2 N-caustic soda. Extraction was conducted three times with 50 parts of benzene and the extract was dried over anhydrous sodium sulfate. Benzene was distilled off and the residue was dried under reduced pressure to form a solid. The solid was dissolved in 50 parts of anhydrous ether and a hydrochloric acid gas was blown into the solution to form a hydrochloride. The hydrochloride was recrystallized twice from a mixed solvent of ethyl acetate and ether. As a result 11.2 parts of 1-(2'-propenylphenoxy)-3-(tert.-butylamino)-2-propanol hydrochloride melting at 144°–145° C. were obtained. The results of infra-red spectrum analysis and ultraviolet absorption analysis of the resulting hydrochloride are as follows:

IR $\nu_{max}^{KBr}$ (cm$^{-1}$): 3340, 2990, 2800, 1491, 1454, 1235, 746

UV $\lambda_{wax}^{EtOH}$ m$\mu(\epsilon)$: 250(1.47×10$^4$), 296(4.22×10$^3$)

EXAMPLE 4

Preparation of 1-($\alpha$-naphthoxy)-3-(tert.-butylamino)-2-propanol hydroxide

To a mixture of 6.5 parts of 1-(tert.-butyl)-3-azetidinol and 7.9 parts of $\alpha$-naphthol 0.2 part of potassium hydroxide was added, and the mixture was heated at 160° C. for 24 hours. The reaction mixture was cooled and then dissolved in 100 parts of ether. The solution was washed twice with 50 parts of 2 N-sodium hydroxide aqueous solution and extracted three times with 50 parts of 2 N-hydrochloric acid aqueous solution. The extract was washed with 50 parts of ether and made alkaline by addition of 2 N-sodium hydroxide aqueous solution. Extraction was conducted three times with 50 parts of benzene, and the extract was dried over anhydrous sodium sulfate. Then benzene was distilled off and the residue was solidified by drying under reduced pressure. The solid residue was subjected to distillation under reduced pressure. As a result, 5 parts of 1-($\alpha$-naphthoxy)-3-(tert.-butylamino)-2-propanol boiling at 175°–180° C. under 1.5 mm Hg were obtained. A part of the product was dissolved in 5 parts of anhydrous ether and the product was converted to a hydrochloride by adding a hydrochloric acid gas to the resulting ether solution. The hydrochloride was recrystallized twice from a mixed solvent of ethyl acetate and ether. As a result, 1-($\alpha$-naphthoxy)-3-(tert.-butylamino)-2-propanol hydrochloride having a melting point of 182°–184° C. was obtained.

EXAMPLE 5

To a mixture of 11.5 parts of 1-(iso-propyl)-3-azetidinol and 15.8 parts of $\alpha$-naphthol 0.2 part of potassium hydroxide was added, and the mixture was heated under nitrogen gas at 160° C. for 20 hours. The reaction mixture was cooled and then extracted with ether. The ether extract was washed with 2 N-NaOH aqueous solution and then with water. The liquor was dried over anhydrous sodium sulfate and the solvent was distilled off. The residue was recrystallized from cyclohexane or subjected to distillation under reduced pressure. As a result, 19.6 parts of 1-($\alpha$-naphthoxy)-3-(iso-propylamino)-2-propanol having a melting point of 94°–96° C. and a boiling point of 158°–159° C. under 2.5 mm Hg were obtained. The yield was 76%. The results of infra-red spectrum analysis of the product are as follows:

IR(KBr) $\nu$cm$^{-1}$: 3260, 2960, 2910, 1580, 1455, 1400, 1270, 1105, 1065, 790, 765

EXAMPLE 6

To a mixture of 10.2 parts of 1-ethyl-3-azetidinol and 14.4 parts of $\alpha$-naphthol 0.2 part of potassium hydroxide was added, and the mixture was heated under nitrogen gas at 160° C. for 18 hours. The reaction mixture was cooled and extracted with ether. The ether extract was washed with 2 N-NaOH aqueous solution and then with water. The liquor was dried over anhydride sodium sulfate and the solvent was distilled off. The residue was recrystallized from cyclohexane to yield 17.2 parts of 1-($\alpha$-naphthoxy)-3-ethylamino-2-propanol. The melting of the product was 106°–107° C. The yield was 70%.

EXAMPLE 7

1-(isopropyl)-3-azetidinol and $\alpha$-naphthol were reacted in the same manner as in Example 6 to form 1(-$\alpha$-naphthoxy)-3-(iso-propylamino)-2-propanol. Then the propanol was dissolved in anhydrous ether and was converted to a hydrochloride by blowing a hydrochloric acid gas into the resulting solution. As a result, 1-($\alpha$-naphthoxy)-3-(iso-propylamino)-2-propanol hydrochloride melting at 162°–164° C. was obtained.

EXAMPLE 8

To a mixture of 14.2 parts of 1-(sec.-butyl)-3-azetidinol and 14.4 parts of $\alpha$-naphthol 0.2 part of sodium hydroxide was added and the mixture was heated under nitrogen gas at 160° C. for 22 hours. The reaction mixture was cooled and then extracted with ether. The extract was washed with 2 N-NaOH aqueous solution and then with water. The liquid was dried over anhydrous sodium sulfate and the solvent was distilled off. Recrystallization of the residue gave 15.5 parts of 1-($\alpha$-naphthoxy)-3-(sec.-butylamino)-2-propanol melting at 57°–59° C. The yield was 57%.

EXAMPLE 9

1-(iso-propyl)-3-azetidinol and 5,6,7,8-tetrahydro-1-naphthol were reacted in the same manner as in Example 1 to form 1-(5',6',7',8'-tetrahydro-1'-naphthoxy)-3-(iso-propylamino)-2-propanol. Then the product was converted to 1-(5',6',7',8'-tetrahydro-1'-naphthoxy)-3-(iso-propylamino)-2-propanol hydrochloride melting at 157°–159° C. by blowing of a hydrochloric acid gas. The yield was 73%.

EXAMPLE 10

To a mixture of 5.8 parts of 1-(iso-propyl)-3-azetidinol and 9.3 parts of 1-phenoxyphenol 0.1 part of sodium hydroxide was added, and the mixture was heated under nitrogen gas at 160° C. for 18 hours. The reaction mixture was cooled and extracted with ether. The extract was washed in water and then the solvent was distilled off. Recrystallization of the residue gave 16.1 parts of 1-(p-phenoxyphenoxy)-3-(iso-propylamino)-2-propanol having a melting point of 72°–74° C. The yield was 58%.

EXAMPLE 11

1-(iso-propyl)-3-azetidinol and m-cresol were reacted in the same manner as in Example 6 to yield 1-(3'-methylphenoxy)-3-(iso-propylamino)-2-propanol melting at 80°–82° C. The yield was 81%.

EXAMPLE 12

1-(iso-propyl)-3-azetidinol and 2,3-dichlorophenol were reacted in the same manner as in Example 6 to yield 1-(2',3'-dichlorophenoxy)-3-(iso-propylamino)-2-propanol melting at 94°–96° C. The yield was 54%.

EXAMPLE 13

1-(sec.-butyl)-3-azetidinol and m-cresol were reacted in the same manner as in Example 6 to yield 1-(3-methylphenoxy)-3-(sec.-butylamino)-2-propanol. A hydrochloric acid gas was blown to yield 1-(3-methylphenoxy)-3-(sec.-butylamino)-2-propanol hydrochloride melting at 159°–160° C. The yield was 69%.

EXAMPLE 14

When 1-(iso-propyl)-3-azetidinol and 2-allyloxyphenol were reacted in the same manner as in Example 6, 1-(2-allyloxyphenoxy)-3-(iso-propylamino)-2-propanol melting at 76°–79° C. The yield was 48%.

EXAMPLE 15

To a mixture of 11.6 parts of 1-(iso-propyl)-3-azetidinol and 13.3 parts of 5-hydroxyindol was added 0.2 part of sodium hydroxide was added, and the mixture was heated under nitrogen gas at 160° C. for 20 hours. The reaction mixture was cooled and then extracted with ether. The extract was dried over anhydrous sodium sulfate and the solvent was distilled off. As a result, 13.5 parts of 1-(5'-indolyloxy)-3-(iso-propylamino)-2-propanol in the form of needles melting at 183°–185° C. were obtained.

EXAMPLE 16

When 6.1 parts of 1-(iso-propyl)-3-azetidinol and 6 parts of 5-hydroxy-1,4-benzodioxane were reacted under nitrogen gas in the same manner as in Example 6, 6.4 parts of 1-(1',4'-benzodioxanoyl-5'-oxy)-3-(iso-propylamino)-2-propanol melting at 90°–91° C. were obtained.

EXAMPLE 17

To a mixture of 6.2 parts of 1-(iso-propyl)-3-benzyloxyazetidine and 28 parts of phenol 1.5 parts of potassium hydroxide was added, and the mixture was heated at 180° C. for 6 hours. The reaction mixture was cooled and 100 parts of ether were added thereto. The excessive phenol was extracted with 2 N-sodium hydroxide aqueous solution and removed. The remaining ether layer was washed in water and dried over anhydrous sodium sulfate. After distillation of ether, the residue was successively subjected to distillation to yield 7.6 parts of 1-phenoxy-2-benzyloxy-3-(iso-propylamino)-propane boiling at 158°–160° C. under 2 mm Hg. The yield was 85%. Results of infra-red spectrum analysis and nuclear magnetic resonance analysis of the product are as follows:

IR $\nu_{max}^{film}$: 3010 cm$^{-1}$, 2950 cm$^{-1}$, 1600 cm$^{-1}$, 1500 cm$^{-1}$, 1260 cm$^{-1}$, 760 cm$^{-1}$, 700 cm$^{-1}$.

NMR (CCl$_4$): 1.0 ppm (6H.d), 1.1 ppm (1H.s), 2.7 ppm (1H.m), 2.75 ppm (2H.d), 3.9 ppm (1H.m), 4.0 ppm (2H.s), 4.65 ppm (2H.d), 6.9 ppm (5H.m), 7.25 ppm (5H.s).

EXAMPLE 18

To a mixture of 6.6 parts of 1-tert.-butyl-3-benzyloxyazetidine and 36 parts of 2,3-xylenol 1.5 parts of sodium hydroxide was added, and the mixture was heated at 180° C. for 16 hours. The reaction mixture was cooled and 100 parts of ether were added thereto. Excessive 2,3-xylenol was removed by extraction with 2 N-sodium hydroxide aqueous solution, and the remaining ether layer was washed in water and dried over anhydrous sodium sulfate. After distillation of ether, the residue was further subjcted to distillation to yield 8.4 parts of 1-(2',3'-xyloxy)-2-benzyloxy-3-(tert.-butylamino)propane boiling at 164°–167° C. under 1 mm Hg. The yield was 82%.

EXAMPLE 19

To a mixture of 6.2 parts of 1-(iso-propyl)-3-benzyloxyazetidine and 43 parts of α-naphthol 1.5 parts of sodium hydroxide was added, and the mixture was heated at 200° C. for 16 hours. The reaction mixture was cooled, and 100 parts of ether were added thereto. Excessive α-naphthol was removed by extraction with 2 N-sodium hydroxide aqueous solution. The remaining ether layer was washed in water and dried over anhydrous sodium sulfate. After distillation of ether, the residue was subjected to distillation to yield 8.3 parts of 1-(α-naphthoxy)-2-benzyloxy-3-(iso-propylamino)-propane boiling at 192°–195° C. The yield was 79%.

EXAMPLE 20

To a mixture of 1.6 parts of 1-iso-propyl-3-methoxymethoxyazetidine and 9.4 parts of phenol 0.5 part of sodium hydroxide was addded, and the mixture was heated at 180° C. for 6 hours. The reaction mixture was cooled and 100 parts of ether were added thereto. Excessive phenol was removed by extraction with 2 N-sodium hydroxide aqueous solution, and the remaining ether layer was washed in water and dried over anhydrous sodium sulfate. After distillation of ether, the residue was subjected to distillation to yield 1.6 parts of 1-phenoxy-2-methoxymethoxy-3-(iso-propylamino)-propane boiling at 146°–149° C. under 2 mm Hg. The yield was 67%.

EXAMPLE 21

A 100-ml flask was charged with 29 g of α-naphthol, 20.5 g of 1-(iso-propyl)-3-benzyloxyazdtidine and 0.6 g of potassium hydroxide, and they were heated and reacted at 240° C. for 20 hours on a mantle heater. The reaction mixture was cooled and poured into 300 ml of 10%-NaOH aqueous solution. Then the mixture was extracted with ether and the ether layer was further extracted with 10%-HCl aqueous solution, and the resulting aqueous solution was made alkaline by careful addition of anhydrous sodium carbonate. Then, the liquor was extracted with ether and subjected to customary post-treatments, followed by distillation under reduced pressure. As a result, 25 g of 1-(α-naphthoxy)-2-benzyloxy-3-(iso-propylamino)-propane boiling at 191°–195° C. were obtained. Results of infra-red spectrum analysis and nuclear magnetic resonance analysis of the product are as follows:

IR $\nu_{max}^{KBr}$: 3300 cm$^{-1}$, 3050 cm$^{-1}$, 2950 cm$^{-1}$, 1590 cm$^{-1}$, 1410 cm$^{-1}$, 1285 cm$^{-1}$, 1260 cm$^{-1}$, 1140 cm$^{-1}$, 800 cm$^{-1}$, 780 cm$^{-1}$, 745 cm$^{-1}$, 710 cm$^{-1}$.

NMR (CCl$_4$): 1.02 ppm (6H.d), 1.30 ppm (1H.s), 2.72 ppm (1H.m), 2.85 ppm (2H.d), 3.8–4.3 ppm (3H.m), 4.7 ppm (2H.d), 6.6–8.3 ppm (7H.m), 7.24 ppm (5H.s).

EXAMPLE 22

24.4 g of 2,3-xylenol, 21.9 g of 1-tert.-butyl-3-benzyloxyazetidine and 0.6 g of potassium hydroxide were added to a 100-ml flask, and they were heated at 220° C. for 18 hours. The reaction mixture was cooled and poured into 10%-NaOH aqueous solution. The the mixture was extracted with ether, and the ether extract was acidified with 20% hydrochloric acid aqueous solution, and the extract was stirred for a while. Crystals were formed which were recovered by filtration and recrystallized from methanol. As a result, 32 g of 1-(2,3-dimethylphenoxy)-2-benzyloxy-3-(tert.-butylamino)-propane hydrochloride were obtained in the form of colorless needles melting at 186° C. The so obtained hydrochloride was added to 20% aqueous solution of sodium hydroxide, and the mixture was extracted with ether. The extract was dried over anhydrous sodium sulfate and ether was removed therefrom by distillation. The residue was subjected to distillation under reduced pressure. As a result, 27 g of 1-(2′,3′-dimethylphenyloxy)-2-benzyloxy-3-(tert.-butylamino)-propane boiling at 165°–170° C. under 1 mm Hg were obtained. The results of infra-red spectrum analysis and nuclear magnetic resonance analysis are as follows:

IR $\nu_{max}^{KBr}$: 3300 cm$^{-1}$, 3020 cm$^{-1}$, 2950 cm$^{-1}$, 1595 cm$^{-1}$, 1470 cm$^{-1}$, 1280 cm$^{-1}$, 1120 cm$^{-1}$, 780 cm$^{-1}$, 745 cm$^{-1}$, 710 cm$^{-1}$.

NMR (CCl$_4$): 1.04 ppm (1H.s), 2.14 ppm (3H.s), 2.24 ppm (3H.s), 2.76 ppm (2H.d), 3.7–4.1 ppm (3H.m), 4.66 ppm (2H.s), 6.55–7.1 ppm (3H.m), 7.23 ppm (5H.s), 1.0 ppm (9H.s).

EXAMPLE 23

1-(tert.-butyl)-3-azetidinol and 5,6,7,8-tetrahydro-α-naphthol were reacted in the same manner as in Example 1 to form 1-(5,6,7,8-tetrahydro-α-naphthoxy)-3-(tert.-butylamino)-2-propanol. A hydrochloric acid gas was blown into the obtained propanol. As a result, 1-(5,6,7,8-tetrahydro-1-naphthoxy)-3-(tert.-butylamino)-2-propanol hydrochloride having a melting point of 148°–150° C. was obtained. The yield was 70%.

EXAMPLE 24

Synthesis of 1-(α-naphthoxy)-2-benzyloxy-3-(tert.-butylamino)propane and the hydrochloride thereof A mixture of 17.3 parts of α-naphthol, 21.9 parts of 1-(tert.-butyl)-3-benzyloxyazetidine and 1.1 parts of potassium hydroxide was heated under nitrogen gas at 180° C. for 8 hours with agitation. The reaction mixture was cooled and dissolved in 100 parts of ether. The solution was washed with 2 N-sodium hydroxide aqueous solution. When 100 parts of 2 N-hydrochloric acid aqueous solution were added to the ether solution, crystals were formed. The crystals were recovered, washed with 50 parts of ether, dried and recrystallized from a mixture of ethanol and ether. As a result, 35.2 parts of 1-(α-naphthoxy)-2-benzyloxy-3-tert.-butylamino)-propane hydrochloride melting at 171°–173° C. were obtained. The yield was 88%. The results of infra-red spectrum analysis of the hydrochloride are as follows:

IR $_{KBrdisk}{cm}^{-1}$: 3400, 2980, 2750, 1640, 1605, 1280, 1240, 1200, 1130, 750, 760.

Crystals of the so obtained hydrochloride were dissolved in 100 parts of 2 N-sodium hydroxide aqueous solution and extracted with 100 parts of ether. The ether solution was dried over anhydrous sodium sulfate, and ether was removed by distillation. The residue was subjected to distillation to yield 29.4 g of 1-(α-naphthoxy)-2-benzyloxy-3-(tert.-butylamino)-propane boiling at 183°–188° C. under 1 mm Hg. The yield was 81%. The results of infra-red spectrum analysis and nuclear magnetic resonance analysis of the product are as follows:

IR$_{cm-1}^{Film}$: 3040, 2950, 1585, 1460, 1400, 1280, 1245, 1150, 800, 780, 740, 705.

NMR$_{ppm}^{CDCl_3}$: (1.09. 9H.s) (1.33. 1H.s) (2.90. 2H.d) (4.20. 1H.m) (4.25. 2H.s) (4.78. 2H.d) (6.7–8.4. 12H.m).

EXAMPLE 25

Synthesis of 1-(β-naphthoxy)-2-benzyloxy)-(iso-propylamino)-propane and the hydrochloride thereof A mixture of 17.3 parts of β-naphthol, 20.5 parts of 1-(iso-propyl)-3-benzyloxyazetidine, and 1.1 parts of potassium hydroxide was heated under nitrogen gas at 180° C. for 8 hours with agitation. The reaction mixture was cooled and dissolved in 100 parts of ether. The solution was washed with 50 parts of 2 N-sodium hydroxide aqueous solution and dried over anhydrous sodium sulfate. Ether was distilled off and the residue was subjected to distillation to yield 29.3 parts of 1-(β-naphthoxy)-2-benzyloxy-3-(iso-propylamino)-propane boiling at 185°–190° C. under 1 mm Hg. The yield was 84%. The results of infra-red spectrum analysis and nuclear magnetic resonance analysis of the product are as follows:

IR$_{cm-1}^{Film}$: 3050, 2960, 1635, 1610, 1465, 1280, 1230, 1190, 1130, 350, 760, 710.

NMR$_{ppm}^{CDCl_3}$: (1.03. 6H.d) (1.51. 1H.s) (2.80. 1H.m) (2.85. 2H.d) (4.1. 1H.m) (4.14 2H.s) (4.71. 2H.d) (7.05–7.80. 12H.m).

The 1-(β-naphthoxy)-2-benzyloxy-3-(iso-propylamino)-propane was dissolved in anhydrous ether, and the solution was acidified with etherical hydrochloric acid. Crystals were formed and recrystallization from a mixture of ethanol and ether gave the intended hydrochloride melting at 135°–137° C. The results of infra-red spectrum analysis of the hydrochloride are as follows:

IR$_{KBr}^{cm-1}$: 3380, 2920, 2650, 1590, 1460, 1405, 1280, 1200, 1120, 1020, 850, 765, 715.

EXAMPLE 26

To 5 g of 2-benzyloxy-3-(iso-propylamino)-1-naphthoxypropane 10 ml of methanol were added. Then 10 ml of ethanol containing Raney-nickel (W-1) were added to the above mixture in an autoclave. The hydrogen pressure in the autoclave was maintained at 100 kg/cm$^2$ and the hydrogenation was conducted at 40° C. for 8 hours. The reaction mixture was cooled and the catalyst was removed by filtration. When the filtrate was concentrated, 3.5 g of 3-(iso-propylamino)-1-(5',6',7',8'-tetrahydro-1-naphthoxy)-2-propanol having a melting point of 83°–85° C. were obtained. The results of infra-red spectrum analysis of the product are as follows:

IR $\nu_{cm^{-1}}^{KBr}$: 3400, 3250, 2910, 1595, 1465, 1270, 1099, 770

The hydrochloride of the above product was prepared by a customary technique. The hydrochloride had a melting point of 162°–163° C. The results of infra-red spectrum analysis of the hydrochloride are as follows:

IR $\nu_{cm^{-1}}^{KBr}$: 3300, 2910, 1590, 1465, 1270, 1110, 995, 780

EXAMPLE 27

To 7.7 g of 2-benzyloxy-3-(tert.-butylamino)-1-naphthoxypropane 15 ml of methanol were added, and 8 ml of ethanol containing Raney-nickel (W-1) were added to the mixture in an autoclave. The hydrogen pressure in the autoclave was maintained at 100 kg/cm$^2$ and the hydrogenation was conducted at 45° C. for 7 hours. The reaction mixture was cooled and the catalyst was removed by filtration. The filtrate was concentrated and the residue was dissolved in an aqueous solution of hydrochloric acid. The aqueous solution was subjected to concentration under reduced pressure, and the residue was recrystallized from a mixture of ethyl acetate and ether. As a result, 6.3 g of 3-(tert.-butylamino)-1-(5',6',7',8'-tetrahydro-1-naphthoxy)-2-propanol hydrochloride melting at 148°–150° C. were obtained.

EXAMPLE 28

21.9 parts of 2-benzyloxy-1,3-dichloro-propane and 77.5 parts of monomethylamine (40% aqueous solution) were added to an autoclave and they were heated at 90° C. for 48 hours with agitation. The reaction mixture was cooled and 120 parts of 2 N-NaOH aqueous solution were added thereto. Then the mixture was heated to distill off excessive monomethylamine. The remaining liquor was extracted twice with 200 parts of ether, and the extract was washed with 100 parts of water, extracted with 100 parts of 2 N-HCl aqueous solution and further extracted with 50 parts of 2 N-HCl aqueous solution. The water layers were combined, washed with 50 parts of ether and made sufficiently alkaline with 2 N-NaOH aqueous solution. The liquor was extracted twice with 100 parts of ether, and the ether extract was washed in 50 parts of water and dried over anhydrous soduim sulfate. The solvent was distilled off and the residue was subjected to distillation to yield 8.3 parts of 3-benzyloxy-1-methylazetidine boiling at 80°–82° C. The yield was 47%. The results of infra-red spectrum analysis and nuclear magnetic resonance analysis of the product are as follows:

IR (CCl$_4$) $\nu$cm$^{-1}$: 2940, 2825, 1445, 1350, 1195, 1180, 1100, 695

NMR (CCl$_4$) ppm:

22.28, 3H(S), \\NCH$_3$;

-continued 2.72, 2H(t), —C—H;

3.46, 2H(t), —C—H;

3.99, 1H(m), —OCH;

4.30, 2H(S), —CH$_2$—;

7.18, 5H(S), 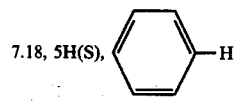—H

The starting compound, 2-benzyloxy-1,3-dichloro-propane is described in Zh. Org. Khim. 3(1), 74–78 (1967).

EXAMPLE 29

21.9 parts of 2-benzyloxy-1,3-dichloro-propane, 45.1 parts of monoethylamine and 45.1 parts of water were added to an autoclave and the mixture was heated at 90° C. for 48 hours with agitation. The reaction mixture was cooled and treated in the same manner as in Example 29, followed by distillation under reduced pressure. As a result, 11.6 parts of 3-benzyloxy-1-ethylazetidine boiling at 73°–74° C. under 2 mm Hg were obtained. The yield was 61%. The results of infra-red spectrum analysis and nuclear magnetic resonance analysis of the product are as follows:

IR (CCl$_4$) $\nu$cm$^{-1}$: 2950, 2850, 1450, 1390, 1360, 1210, 1195, 1130, 1020, 700

NMR (CCl$_4$) ppm: 0.88, 3H(t), —CH$_3$;

2.36, 2H(g), \\NCH$_2$—;

2.67, 2H(t), —C—H;

3.44, 2H(t), —C—H;

4.20, 1H(m), —OCH;

4.31, 2H(s), —CH$_2$;

7.18, 5H(S), 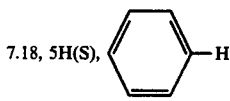

EXAMPLE 30

21.9 Parts of 2-benzyloxy-1,3-dichloropropane, 59.1 parts of n-propylamine and 59.1 parts of water were added to an autoclave, and the mixture was heated at 90° C. for 48 hours with agitation. The reaction mixture was cooled and treated in the same manner as in Example 29, followed by distillation under reduced pressure. As a result, 13.7 parts of 3-benzyloxy-1-(n-propyl)azetidine boiling at 101°–103° C. under 2 mm Hg were obtained. The yield was 67%. The results of infra-red spectrum analysis and nuclear magnetic resonance analysis of the product are as follows:

IR (CCl$_4$) νcm$^{-1}$: 2925, 1450, 1380, 1355, 1200, 1110, 1000, 695

NMR (CCl$_4$) ppm:  0.84, 3H(t), —CH$_3$;
 1.20, 2H(m), —CH$_2$—;

2.30, 3H(t), 

2.68, 2H(t), —CH; 

3.43, 2H(t), —CH; 

4.02, 1H(m), —OCH; 

4.31, 2H(S), —CH$_2$—;

7.17, 5H(S), 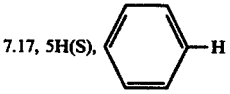

EXAMPLE 31

21.9 Parts of 2-benzyloxy-1,3-dichloro-propane, 59.1 parts of iso-propylamine and 59.1 parts of water were added to an autoclave, and the mixture was heated at 90° C. for 48 hours with agitation. The reaction mixture was cooled and treated in the same manner as in Example 29, followed by distillation under reduced pressure. As a result, 17.4 parts of 3-benzyloxy-1-(iso-propyl)azetidine boiling at 105°–107° C. under 2 mm Hg were obtained. The yield was 85%. The results of infra-red spectrum analysis and nuclear magnetic resonance analysis of the product are as follows:

IR (CCl$_4$) νcm$^{-1}$: 2960, 2825, 1450, 1355, 1185, 1130, 1050, 1010, 700

NMR (CCl$_4$) ppm:  0.85, 6H(d), —CH$_3$;

2.20, 1H(m), 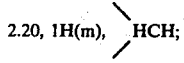

2.70, 2H(t), —CH; 

3.43, 2H(t), —CH; 

4.00, 1H(m), —OCH; 

4.32, 2H(S), —CH$_2$—;

7.18, 5H(S), 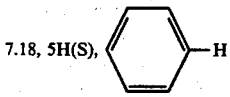

EXAMPLE 32

21.9 Parts of 2-benzyloxy-1,3-dichloro-propane, 71.3 parts of tert.-butylamine and 50 parts of water were added to an autoclave and the mixture was heated at 90° C. for 48 hours with agitation. The reaction mixture was cooled and treated in the same manner as in Example 29, followed by distillation under reduced pressure. As a result, 17.5 parts of 3-benzyloxy-1-(tert.-butyl)azetidine boiling at 94°–96° C. under 2 mm Hg were obtained. The yield was 80%. The results of infra-red spectrum analysis and nuclear magnetic resonance analysis are as follows:

IR (CCl$_4$) νcm$^{-1}$: 2950, 1450, 1360, 1225, 1150, 1060, 690

NMR (CCl$_4$) ppm:  0.89, 9H(S), —CH$_3$;

2.95, 2H(t), —CH; 

3.33, 2H(t), —CH; 

4.00, 1H(m), —OCH; 

4.30, 2H(S), —CH$_2$—;

7.17, 5H(S), 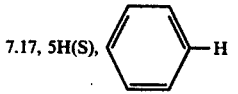

EXAMPLE 33

A solution of 4.1 parts of 3-benzyloxy-1-(iso-propyl)azetidine in 30 parts of ethanol was added to an autoclave together with 2 parts of Raney nickel as catalyst, and under a hydrogen gas pressure of 100 atmospheres, the mixture was agitated at 40° C. for 15 hours to perform the reduction. The catalyst was removed by filtration and the remaining ethanol solution was concentrated to dryness. The resulting oily substance was subjected to distillation under reduced pressure, or dissolved in n-hexane and cooled. As a result, 1.9 parts of 1-(iso-propyl)-3-azetidinol in the form of white crystals were obtained. The product had a melting point of 56°–57° C. and a boiling point of 75°–76° C. under 3 mm Hg. The yield was 82%. The results of infra-red spectrum analysis and nuclear magnetic resonance analysis of the product are as follows:

IR (KBr) $\nu$cm$^{-1}$: 3100, 2960, 2825, 1465, 1410, 1340, 1210, 1160, 745

NMR (CCl$_4$) ppm:  0.90, 6H(d), —CH$_3$;

2.28, 1H(m), $\diagdown$NCH;

3.73, 2H(t), —CH;

3.46, 2H(t), —CH;

4.20, 1H(m), —OCH;

5.75, 1H(S), —OH

EXAMPLE 34

A solution of 4.4 parts of 3-benzyloxy-1-(tert.-butyl-)azetidine in 30 parts of ethanol was added to an autoclave together with 2 parts of Raney nickel as catalyst. Under a hydrogen gas pressure of 100 atmospheres, the mixture was stirred at 40° C. for 15 hours to perform the reduction. The catalyst was separated by filtration, and the remaining ethanol solution was concentrated to dryness. The resulting oily substance was dissolved in n-hexane and cooled. As a result 2.0 parts of 1-(tert.-butyl)-3-azetidinol melting at 42°–43° C. The yield was 76%. The results of infra-red spectrum analysis and nuclear magnetic resonance analysis of the product are as follows:

IR (KBr) $\nu$cm$^{-1}$: 3200, 2925, 1460, 1360, 1225, 1145, 1100, 980, 730

NMR (CCl$_4$) ppm:  0.97, 9H(S), —CH$_3$;

3.04, 2H(t), —CH;

3.38, 2H(t), —CH;

4.37, 1H(m), —OCH;

6.30, 1H(S), —OH

EXAMPLE 35

33.7 Parts of 2-(p-methoxybenzyloxy)-1,3-dibromo-propane, 70 parts of monomethylamine and 70 parts of water were added to an autoclave, and the mixture was heated at 90° C. for 48 hours with agitation. The reaction mixture was cooled and treated in the same manner as in Example 29, followed by distillation under reduced pressure. As a result, 11.7 parts of 3-(p-methoxybenzyloxy)-1-methylazetidine boiling at 85°–87° C. under 2 mm Hg were obtained.

EXAMPLE 36

11 Parts of 2-benzyloxy-1,3-dibromo-propane, 30 parts of iso-propylamine and 30 parts of water were added to a stainless autoclave, and the mixture was heated at 80° C. for 2 hours with agitation. The reaction mixture was cooled and treated in the same manner as in Example 29, followed by distillation under reduced pressure. As a result, 18 parts of 3-benzyloxy-1-(iso-propyl)azetidine boiling at 104°–107° C. under 2 mm Hg were obtained.

EXAMPLE 37

Synthesis of
1-($\beta$-naphthoxy)-2-benzyloxy-3-(tert.-butylamino)-propane and the hydrochloride thereof A mixture of 17.3 parts of $\beta$-naphthol, 21.9 parts of 1-(tert.-butyl)-3-benzyloxy-azetidine and 1.1 parts of potassium hydroxide was heated under nitrogen gas at 180° C. for 8 hours with agitation. The reaction mixture was cooled and treated in the same manner as in Example 18 to form crystals. Recrystallization from a mixture of ethanol and ether gave 33.4 parts of 1-($\beta$-naphthoxy)-2-benzyloxy-3-(tert.-butylamino)-propane hydrochloride melting at 165°–167° C. The yield was 83.5%. The results of infra-red spectrum analysis of the hydrochloride are as follows:

IR$_{cm-1}^{KBr}$: 3400, 2980, 2750, 1595, 1410, 1400, 1110, 800, 760, 715

The so obtained hydrochloride was treated in the same manner as in Example 5 to obtain 28.9 parts of 1-($\beta$-naphthoxy)-2-benzyloxy-3-(tert.-butylamino)-propane boiling at 188°–195° C. under 1 mm Hg. The yield was 72%. The results of infra-red spectrum analysis and nuclear magnetic resonance analysis of the product are as follows:

IR$_{cm-1}^{Film}$: 3050, 2950, 1635, 1610, 1465, 1280, 1235, 1195, 1130, 850, 760, 710.

NMR$_{ppm}^{CDCl_3}$: (1.09. 9H.s) (13.39. 1H.s) (2.85. 2H.d) (4.1. 1H.m) (4.18. 2H.s) (4.73. 2H.d) (7.1–7.85. 12H.m).

EXAMPLE 38

Preparation of
1-(p-aminophenoxy)-3-(tert.-butylamino)-2-propanol

A mixture of 21.8 g of p-aminophenol, 22 g of 1-(tert.-butyl)-3-azetidinol and 0.73 g of potassium hydroxide was heated under nitrogen gas at 140° C. for 8 hours with agitation. The reaction mixture was cooled and dissolved in concentrated hydrochloric acid and the solution was extracted with ether. The hydrochloric acid aqueous solution was made alkaline with 10% -NaOH aqueous solution and then extracted with ether. The ether solution was washed with water and dried over anhydrous sodium sulfate. Then ether was distilled off and the residue was recrystallized from benzene. as a result, 8 g of 1-(p-aminophenoxy)-3-(tert.-butylamino)-2-propanol melting at 125°-127° C. were obtained. The results of infra-red spectrum analysis and nuclear magnetic resonance analysis are as follows:

$NMR_{ppm}^{CDCl_3}$: 1.12 (9H.s), 2.74 (2H.m), 2.96 (4H.m), 3.90 (3H.d+m), 6.68 (4H.d)

$IR_{cm^{-1}}^{KBr}$: 3400, 3300, 2960, 1640, 1520, 1465, 1350, 1250, 1120, 1040, 890, 840, 690

EXAMPLE 39

Synthesis of 1-(p-hydroxyphenoxy)-3-(tert.-butylamino)-2-propanol hydrochloride

A mixture of 11 parts of hydroquinone, 6.5 parts of 1-(tert.-butyl)-3-azetidinol and 0.3 part of potassium hydroxide was heated under nitrogen gas at 140° C. for 8 hours with agitation. The reaction mixture was cooled and dissolved into 50 parts of 4 N-hydrochloric acid aqueous solution. The resulting solution was washed with 50 parts of chloroform. The water layer was acidified with concentrated hydrochloric acid, evaporated and solidified. The residue was dissolved in isopropyl alcohol and filtered. The filtrate was decolored with active carbon and allowed to cool. As a result, 6.9 parts of 1-(p-hydroxyphenoxy)-3-(tert.-butylamino)-2-propanol hydrochloride melting at 201°-203° C. were obtained. The yield was 58%. The results of infra-red spectrum analysis and nuclear magnetic resonance analysis of the resulting hydrochloride are as follows:

$IR_{cm^{-1}}^{KBr}$: 3300, 2980, 2800, 1515, 1455, 1400, 1265, 1220, 1105, 1010, 850, 790

$NMR_{ppm}^{(CD_3)_2SO}$: (1.33. 9H.s) (3.0. 2H.m) (3.35. 1H.m) (3.90. 2H.d) (4.2. 1H.m) (6.75. 4H.s) (8.8. 2H.m) (9.04. 1H.s).

EXAMPLE 40

Synthesis of 1-(4-methoxy-1-naphthoxy)-3-(isopropylamino)-2-propanol hydrochloride A mixture of 16.0 parts of 1,4-naphthalenediol 4-methylether, 5.8 parts of 1-(iso-propyl)-3-azetidinol and 0.3 part of potassium hydroxide was heated under nitrogen gas at 140° C. for 8 hours with agitation. The reaction mixture was cooled and dissolved in 50 parts of 4 N-hydrochloric acid aqueous solution, and the solution was extracted with 50 parts of chloroform. The water layer was made alkaline with 10 N-NaCl aqueous solution and washed with 50 parts of chloroform. The water layer was acidified with concentrated hydrochloric acid, and concentrated to dryness. The residue was shaken with ethanol and filtered. The filtrate was mixed with benzene and concentrated to dryness. The residue was dissolved in iso-propyl alcohol and decolored. Then the solution was concentrated and allowed to cool. As a result, 7.5 g of 1-(4-methoxy-1-naphthoxy)-3-(iso-propylamino)-2-propanol hydrochloride melting at 175°-176° C. were obtained. The yield was 48.2%.

EXAMPLE 41

Synthesis of 1-(2,3-dimethyl-4-methoxyphenoxy)-3-(tert.-butylamino)-2-propanol and the hydrochloride thereof A mixture of 9.1 parts of 2,3-dimethyl-4-methoxyphenol, 6.5 parts of 1-(tert.-butyl)-3-azetidinol and 0.3 part of potassium hydroxide was heated under nitrogen gas at 140° C. for 8 hours with agitation. The reaction product was dissolved in 100 parts of 2 N-hydrochloric acid aqueous solution and washed twice with 100 parts of ether. The water layer was made alkaline with 4 N-sodium hydroxide aqueous solution, and the resulting crystals were recovered by filtration and dried. Then the crystals were dissolved in 100 parts of ether and decolored. The decolored liquid was concentrated and allowed to cool. As a result, 10.2 parts of 1-(2',3'-dimethyl-4'-methoxyphenoxy)-3-(tert.-butylamino)-2-propanol melting at 73°-75° C. were obtained. The yield was 72.5%. The results of infra-red spectrum analysis and nuclear magnetic resonance analysis of the product are as follows:

$IR_{cm^{-1}}^{KBr}$: 3450, 3290, 2960, 1500, 1280, 1115, 1105, 820, 760

$NMR_{ppm}^{CD_3Cl}$: (1.14. 9H.s) (2.19. 6H.s) (2.53. 2H.s) (2.81. 2H.m) (3.78. 3H.s) (3.95. 3H.d+m) (6.67. 2H.s).

The so obtained crystals were dissolved in anhydrous ether and a hydrochloric acid gas was blown into the solution to form its hydrochloride. Recrystallization from a mixture of ethanol and ether gave 1-(2',3'-dimethyl-4'-methoxyphenoxy)-3-(tert.-butylamino)-2-propanol hydrochloride melting at 149°-152° C. The results of infra-red spectrum analysis of the hydrochloride are as follows:

$IR_{cm^{-1}}^{KBr}$: 3300, 2990, 2920, 1500, 1400, 1280, 1230, 1130, 1110, 810

EXAMPLE 42

Synthesis of 1-(6'-methoxy-1'-naphthoxy)-3-(isopropylamino)-2-propanol hydrochloride A mixture of 9.5 parts of 6-methoxy-1-naphthol, 5.8 parts of 1-(iso-propyl)-3-azetidinol and 0.3 part of potassium hydroxide was heated under nitrogen gas at 140° C. for 8 hours with agitation. The reaction mixture was treated in the same manner as in Example 1, and when the resulting hydrochloride was recrystallized from iso-propyl alcohol, there was obtained 17.7 parts of 1-(6'-methoxy-1-naphthoxy)-3-(iso-propylamino)-2-propanol hydrochloride melting at 165°-167° C. The yield was 57.5%.

EXAMPLE 43

5-oxo-5,6,7,8-tetrahydro-1-naphthol and 1-tert.-butylazetidinol were reacted in the same manner as in Example 1. Recrystallization from a mixture of methanol and ether gave 1-(5'-oxo-5',6',7',8'-tetrahydro-1-naphthoxy)-3-(tert.-butyl)-2-propanol hydrochloride melting at 224°-226° C.

EXAMPLE 44

5-oxo-5,6,7,8-tetrahydro-2-naphthol and 1-(iso-propyl)-azetidinol were reacted in the same manner as in Example 1. Recrystallization from ethanol gave 1-(5'-oxo-5',6',7',8'-tetrahydro-2-naphthoxy)-3-(iso-propylamino)-2-propanol hydrochloride melting at 168°-169° C.

EXAMPLE 45

A mixture of 21.8 parts of m-aminophenol, 22 parts of 1-(tert.-butyl)-3-azetidinol and 0.7 part of potassium hydroxide was heated under nitrogen gas at 140° C. for 8 hours with agitation. The reaction mixture was cooled and treated in the same manner as in Example 39. Recrystallization from benzene gave 17.2 parts of 1-(3'-aminophenoxy)-3-(tert.-butylamino)-2-propanol in the form of colorless needles melting at 105°–106° C. The yield was 42.3%. The results of infra-red spectrum analysis are as follows:

$IR_{cm-1}^{KBr}$: 3450, 3330, 2960, 1610, 1480, 1335, 1305, 1190, 1100, 760, 690

EXAMPLE 46

To 5 g of 2-benzyloxy-3-(iso-propylamino)-1-naphthoxypropane 10 ml of methanol were added. Then 10 ml of ethanol containing Raney-nickel (W-1) were added to the above mixture in an autoclave. The hydrogen pressure in the autoclave was maintained at 100 kg/cm² and the hydrogenation was conducted at 40° C. for 3 hours. The reaction mixture was cooled and the catalyst was removed by filtration. When the filtrate was concentrated, 3.5 g of 3-(iso-propylamino)-2-benzyloxy-1-(5',6',7',8'-tetrahydro-1-naphthoxy-propane having a boiling point of 165°–168° C. under 0.4 mm Hg were obtained.

The product was identified by NMR spectrum.

What we claim is:

1. A process for the preparation of 1-aryloxy-3-aminopropane derivative expressed by the formula $$Ar-O-CH_2-\underset{\underset{OZ}{|}}{CH}-CH_2-NHR$$

wherein

R is a straight or branched alkyl group of up to 6 carbon atoms or an aralkyl group of 7 to 9 carbon atoms;

Z is a hydrogen atom, an alkoxymethyl group of 1 to 4 carbon atoms in the alkyl moiety or a group represented by the formula

[benzene ring with $(R^9)_n$ substituent and $-CH_2$ group]

wherein $R^9$ is a hydrogen atom or an electron-donor group selected from the group consisting of an alkyl group of 1 to 4 carbon atoms, an alkoxy group of 1 to 4 carbon atoms, a halogen atom and a halogenated alkyl group of 1 to 4 carbon atoms, and n is an integer of 1 to 3; and Ar is a member selected from the group consisting of indolyl groups and 1,4-benzodioxanyl groups, which comprises reacting in a non-aqueous reaction system a tertiary azetidinol derivative expressed by the formula

[Z-O-azetidine ring with N-R]

wherein Z and R are as defined above, with a heterocyclic compound selected from the group consisting of hydroxyindols and hydroxy-1,4-benzodioxanes at a temperature of 130° C. to 250° C. in the absence of a catalyst or in the presence of not more than 1/10 mole of a basic catalyst per mole of the heterocyclic compound.

2. The process according to claim 1 wherein said heterocyclic compound is selected from the group consisting of 5-hydroxyindol and 5-hydroxy-1,4-benzodioxane.

3. The process of claim 1, wherein the reaction is carried out in the presence of 1/100 to 1/10 mole of a caustic alkali per mole of the heterocyclic compound.

4. The process of claim 1 wherein said tertiary azetidinol derivative is selected from the group consisting of 1-(iso-propyl)-3-azetidinol, 1-(sec.-butyl)-3-azetidinol, 1-(sec.-amyl)-3-azetidinol, 1-(tert-butyl)-3-azetidinol, 1-(tert-amyl)-3-azetidinol, 1-ethyl-3-azetidinol and 1-benzyl-3-azetidinol.

5. The process of claim 1 wherein said tertiary azetidinol derivative is selected from the group consisting of 3-benzyloxy-1-methylazetidine, 3-(p-ethoxybenzyloxy)-1-methylazetidine, 3-(p-methylbenzyloxy)-1-methylazetidine, 3-(p-ethylbenzyloxy)-1-methylazetidine, 3-(p-chlorobenzyloxy)-1-methylazetidine, 3-benzyloxy-1-ethyl-azetidine, 3-(p-methoxybenzyloxy)-1-ethylazetidine, 3-(p-ethoxybenzyloxy)-1-ethylazetidine, 3-(p-methylbenzyloxy)-1-ethylazetidine, 3-(p-ethylbenzyloxy)-1-ethylazetidine, 3-(p-chlorobenzyloxy)-1-ethylazetidine, 3-(o-methoxybenzyloxy)-1-ethylazetidine, 3-benzyloxy-1-propylazetidine, 3-benzyloxy-1-(iso-propyl)azetidine, 3-(p-methoxybenzyloxy)-1-(iso-propyl)azetidine, 3-(p-ethoxybenzyloxy)-1-(iso-propyl)azetidine, 3-(p-methylbenzyloxy)-1-(iso-propyl) azetidine, 3-(p-ethylbenzyloxy)-1-(iso-propyl)azetidine, 3-(p-chlorobenzyloxy)-1-(iso-propyl)azetidine, 3-benzyloxy-1-(tert-butyl)azetidine, 3-(p-ethoxybenzyloxy)-1-(tert.-butyl)azetidine, 3-(p-methylbenzyloxy)-1-(tert.-butyl)azetidine, 3-benzyloxy-1-benzyl-azetidine, 3-benzyloxy-1-phenetylazetidine, 3-methoxymethoxy-1-benzylazetidine, 3-ethoxymethoxy-1-benzylazetidine, 3-n-propoxymethoxy-1benzylazetidine, 3-iso-propylazetidine, 3-methoxymethoxy-1-tert.-butylazetidine, 3-(tert.-butoxymethoxy)-1-benzylazetidine, 3-(tert.-butoxymethoxy)-iso-propylazetidine, 3-(tert.-butoxymethoxy)-1-tert.-butylazetidine, 3-(tert.-botoxy)-1-benzylazetidine, 3-(tert.-butoxymethoxy)-iso-propylazetidine, 3-(tert.-butoxymethoxy)-1-tert.-butylazetidine, 3-(tert.-butoxy)-1-benzylazetidine, 3-(tert.-butoxy)-1-iso-propylazetidine, 3-(tert.-butoxy)-1-tert.-butylazetidine, 3-(tert.-amyloxy)-1-benzylazetidine, 3-tert.-amyloxy-1-iso-propylazetidine, 3-(tert.-amyloxy-1-tert.-butylazetidine and 3-(tert.-amyloxy)-1-tert.-amylazetidine.

6. The process according to claim 1, wherein said reaction is carried out at a temperature in the range of from 150° C. to 180° C.

7. The process according to claim 1 which is carried out in the absence of a solvent.

8. The process according to claim 1 wherein the reaction is carried out in a non-polar solvent selected from the group consisting of benzene, xylene and ether.

9. The process according to claim 1 wherein said reaction is carried out in the presence of a basic catalyst selected from the group consisting of solid caustic potash, caustic soda and triethylamine.

10. The process according to claim 2 wherein about 1.2 moles of the heterocyclic compound is reacted per mole of the tertiary azetidinol derivative.

11. The process of claim 1 wherein the reaction is carried out in the presence of not more than 1/10 mole of a basic catalyst per mole of the heterocyclic compound.

12. The process of claim 1 wherein the reaction is carried out in the absence of a catalyst.

* * * * *